(12) United States Patent
Liu et al.

(10) Patent No.: US 10,048,182 B2
(45) Date of Patent: Aug. 14, 2018

(54) ROCK SPECIMEN AND METHOD FOR TESTING PURE SHEAR OF THE SAME

(71) Applicant: Sichuan University, Chengdu (CN)

(72) Inventors: Jianfeng Liu, Chengdu (CN); Heping Xie, Chengdu (CN); Jianhui Deng, Chengdu (CN); Lu Wang, Chengdu (CN); Jianliang Pei, Chengdu (CN); Yong Xiang, Chengdu (CN); Linrui Li, Chengdu (CN); Yu Bian, Chengdu (CN); Huining Xu, Chengdu (CN); Zhiwei Zhou, Chengdu (CN)

(73) Assignee: SICHUAN UNIVERSITY, Chengdu (CN)

( * ) Notice: Subject to any disclaimer, the term of this patent is extended or adjusted under 35 U.S.C. 154(b) by 410 days.

(21) Appl. No.: 14/880,301

(22) Filed: Oct. 12, 2015

(65) Prior Publication Data
US 2016/0103049 A1 Apr. 14, 2016

(30) Foreign Application Priority Data
Oct. 11, 2014 (CN) .......................... 2014 1 0532288

(51) Int. Cl.
| | | |
|---|---|---|
| *G01N 3/20* | (2006.01) | |
| *G01N 3/24* | (2006.01) | |
| *G01N 33/24* | (2006.01) | |
| *G01N 3/08* | (2006.01) | |

(52) U.S. Cl.
CPC .................. *G01N 3/24* (2013.01); *G01N 3/08* (2013.01); *G01N 33/24* (2013.01); *G01N 2203/0298* (2013.01)

(58) Field of Classification Search
CPC ............ G01N 3/08; G01N 3/24; G01N 33/24; G01N 2203/0298
See application file for complete search history.

(56) References Cited

U.S. PATENT DOCUMENTS

| | | | | |
|---|---|---|---|---|
| 4,444,058 A | * | 4/1984 | Ratigan | ..................... G01N 3/08 73/834 |
| 2013/0233536 A1 | * | 9/2013 | Alqam | ..................... G01N 3/00 166/250.01 |

FOREIGN PATENT DOCUMENTS

JP 2008275319 * 11/2008 ............... G01N 3/20

* cited by examiner

*Primary Examiner* — Blake A Tankersley
(74) *Attorney, Agent, or Firm* — Matthias Scholl, PC; Matthias Scholl (57) ABSTRACT

A rock specimen, including a rock body. The rock body includes: an upper part, an upper end face, a first circular groove, a first cylinder, a first circular body, a lower part, a lower end face, a second circular groove, a second cylinder, and a second circular body. The first circular groove is disposed on the upper end face of the rock body and has a circle center coinciding with a center of the upper end face. A method for testing pure shear of the rock specimen, includes: 1) disposing the rock specimen on a test bench of a rock mechanics testing system, allowing the end face of the second circular body to contact the test bench; and 2) operating the rock mechanics testing system, loading a pressure on the rock specimen via the end face of the first cylinder and the end face of the second circular body.

12 Claims, 6 Drawing Sheets

ROCK SPECIMEN AND METHOD FOR TESTING PURE SHEAR OF THE SAME

CROSS-REFERENCE TO RELATED APPLICATIONS

Pursuant to 35 U.S.C. § 119 and the Paris Convention Treaty, this application claims the benefit of Chinese Patent Application No. 201410532288.7 filed Oct. 11, 2014, the contents of which are incorporated herein by reference.

BACKGROUND OF THE INVENTION

Field of the Invention

The invention relates to a rock specimen and a method for testing pure shear of the same.

Description of the Related Art

Shear strength of rocks is a basic parameter in engineering construction. However, conventional methods for measuring the shear strength of rocks often require relatively expensive testing devices.

In addition, it is difficult measure real pure shear (i.e., pure shear when only a single shear stress is exerted on the shear plane of a rock) with conventional shear strength test methods.

SUMMARY OF THE INVENTION

In view of the above-described problems, it is one objective of the invention to provide a rock specimen and an improved method for testing pure shear of the same.

The method allows to conveniently and effectively measure the shear strength of a rock specimen. In addition, the method allows to determine the shear strength of the rock from which the rock specimen originates.

To achieve the above objective, in accordance with one embodiment of the invention, there is provided a first rock specimen. The rock specimen comprises a rock body having a shape of a cylinder or a regular square prism. The rock body comprises: an upper part, an upper end face, a first circular groove, a first cylinder, a first circular body, a lower part, a lower end face, a second circular groove, a second cylinder, and a second circular body. The upper end face is in parallel with the lower end face. The first circular groove is disposed on the upper end face of the rock body and has a circle center coinciding with a center of the upper end face of the rock body. The second circular groove is disposed on the lower end face of the rock body and has a circle center coinciding with a center of the lower end face of the rock body. A width and an inner diameter of the first circular groove are the same as a width and an inner diameter of the second circular groove. A distance between a bottom of the first circular groove and a bottom of the second circular groove is between 10 and 40 mm. The first circular groove divides the upper part of the rock body into the first cylinder located at the center and the first circular body surrounding the first cylinder. The second circular groove divides the lower part of the rock body into the second cylinder located at the center and the second circular body surrounding the second cylinder. A diameter of the first cylinder is the same as a diameter of the second cylinder.

In a class of this embodiment, an end face of the first cylinder and an end face of the first circular body are disposed on a same plane; and an end face of the second cylinder and an end face of the second circular body are disposed on a same plane.

In a class of this embodiment, an end face of the first cylinder is higher than an end face of the first circular body; and an end face of the second cylinder is lower than an end face of the second circular body.

In a class of this embodiment, the distance between the bottom of the first circular groove and the bottom of the second circular groove is between 20 and 30 mm.

In a class of this embodiment, both the diameters of the first cylinder and the second cylinder are between ¼ and ½ of a diameter of the rock body having the shape of the cylinder or a side length of the rock body having the shape of the regular square prism. Both the widths of the first circular groove and the second circular groove are between 2 and 8 mm. A depth of the first circular groove is between 10 and 40 mm. A depth of the second circular groove is between 10 and 40 mm.

In a class of this embodiment, both the widths of the first circular groove and the second circular groove are between 3 and 5 mm. The depth of the first circular groove is between 20 and 30 mm. The depth of the second circular groove is between 20 and 30 mm.

In a class of this embodiment, the distance between the bottom of the first circular groove and the bottom of the second circular groove is between 20 and 30 mm.

In a class of this embodiment, both the diameters of the first cylinder and the second cylinder are between ¼ and ½ of a diameter of the rock body having the shape of the cylinder or a side length of the rock body having the shape of the regular square prism. A height of the first cylinder is between 10 and 40 mm. A distance between the end face of the first cylinder and the end face of the first circular body is not larger than 10 mm. Both the widths of the first circular groove and the second circular groove are between 2 and 8 mm.

In accordance with another embodiment of the invention, there is provided a second rock specimen. The rock specimen comprises a rock body having a shape of a cylinder or a regular square prism. The rock body comprises: an upper part, an upper end face, a first circular groove, a first cylinder, a first circular body, a lower part, a lower end face, a second circular groove, a second cylinder, and a second circular body. The upper end face is in parallel with the lower end face. The first circular groove is disposed on the upper end face of the rock body and has a circle center coinciding with a center of the upper end face of the rock body. The second circular groove is disposed on the lower end face of the rock body and has a circle center coinciding with a center of the lower end face of the rock body. A width of the first circular groove is the same as a width of the second circular groove; an inner diameter of the first circular groove is the same as an outer diameter of the second circular groove. A distance between a bottom of the first circular groove and a bottom of the second circular groove is between 10 and 40 mm. The first circular groove divides an upper part of the rock body into the first cylinder located at the center and the first circular body surrounding the first cylinder. The second circular groove divides a lower part of the rock body into the second cylinder located at the center and the second circular body surrounding the second cylinder. A diameter of the first cylinder is larger than a diameter of the second cylinder.

In a class of this embodiment, an end face of the first cylinder and an end face of the first circular body are disposed on a same plane; and an end face of the second cylinder and an end face of the second circular body are disposed on a same plane.

In a class of this embodiment, an end face of the first cylinder is higher than an end face of the first circular body. An end face of the second cylinder is lower than an end face of the second circular body.

In a class of this embodiment, the distance between the bottom of the first circular groove and the bottom of the second circular groove is between 20 and 30 mm.

In a class of this embodiment, both the widths of the first circular groove and the second circular groove are between 2 and 8 mm. A depth of the first circular groove is between 10 and 40 mm. A depth of the second circular groove is between 10 and 40 mm.

In a class of this embodiment, both the widths of the first circular groove and the second circular groove are between 3 and 5 mm. The depth of the first circular groove is between 20 and 30 mm. The depth of the second circular groove is between 20 and 30 mm.

In a class of this embodiment, the distance between the bottom of the first circular groove and the bottom of the second circular groove is between 20 and 30 mm.

In a class of this embodiment, a height of the first cylinder is between 10 and 40 mm. A distance between the end face of the first cylinder and the end face of the first circular body is not larger than 10 mm. Both the widths of the first circular groove and the second circular groove are between 2 and 8 mm.

A method for manufacturing the rock specimen for pure shear test is described as follows. The rock collected from the field is processed by a rock cutting machine or/and a casing into the rock body having the shape of the cylinder or the rock body having the shape of the regular square prism, and polished by a polishing machine, so that the upper end face and the lower end face of the rock body having the shape of the cylinder or the rock body having the shape of the regular square prism meet the processing accuracy of end faces of the rock specimen for the rock compression test according to the standard test method of engineering rock. The upper end face of the rock body having the shape of the cylinder or the rock body having the shape of the regular square prism is subsequently processed by the casing to form the first circular groove adopting the center of the upper end face of the rock body as the circle center, and the lower end face of the rock body having the shape of the cylinder or the rock body having the shape of the regular square prism is processed to form the second circular groove adopting the center of the lower end face of the rock body as the circle center, so that the first rock specimen for the pure shear test is manufactured. The rock cutting machine is utilized to cut part of the first circular body and part of the second cylinder from the first rock specimen for the pure shear test to form the second rock specimen for the pure shear test.

After the rock is processed into the first rock specimen or the second rock specimen for the pure shear test, the rock specimen is conducted with the pure shear test.

In accordance with still another embodiment of the invention, there is provided a method for testing pure shear of the rock specimen. The method comprises:

1) providing a circular cushion block, disposing the circular cushion block on a test bench of a rock mechanics testing system, where an inner diameter of the circular cushion block is smaller than an inner diameter of the second circular body or an inner diameter of the first circular body and is larger than a diameter of the second cylinder or a diameter of the first cylinder, and an outer diameter of the circular cushion block is larger than a diameter of the rock body having the shape of the cylinder or a side length of the rock body having the shape of the regular square prism; and providing a cylindrical cushion block, in which a diameter of the cylindrical cushion block is larger than the diameter of the first cylinder or the diameter of the second cylinder and smaller than the inner diameter of the first circular body or the inner diameter of the second circular body;

2) disposing the rock specimen on the circular cushion block, allowing a center line of the rock specimen to coincide with a center line of the circular cushion block, and allowing the end face of the second circular body or the end face of the first circular body to contact an end face of the circular cushion block;

3) disposing the cylindrical cushion block on the end face of the first cylinder or the end face of the second cylinder, and allowing a center line of the cylindrical cushion block to coincide with the center line of the rock specimen; and 4) operating the rock mechanics testing system, loading a pressure on the rock specimen via the cylindrical cushion block and the circular cushion block to purely shear the rock specimen.

In a class of this embodiment, both the diameters of the first cylinder and the second cylinder are between ¼ and ½ of the diameter of the rock body having the shape of the cylinder or the side length of the rock body having the shape of the regular square prism. Both the widths of the first circular groove and the second circular groove are between 2 and 8 mm. A depth of the first circular groove is between 10 and 40 mm. A depth of the second circular groove is between 10 and 40 mm.

In accordance with still another embodiment of the invention, there is provided a method for testing pure shear of the rock specimen. The method comprises:

1) disposing the rock specimen on a test bench of a rock mechanics testing system, allowing the end face of the second circular body to contact the test bench; and 2) operating the rock mechanics testing system, loading a pressure on the rock specimen via the end face of the first cylinder and the end face of the second circular body to purely shear the rock specimen.

In a class of this embodiment, both the diameters of the first cylinder and the second cylinder are between ¼ and ½ of a diameter of the rock body having the shape of the cylinder or a side length of the rock body having the shape of the regular square prism. A height of the first cylinder is between 10 and 40 mm. A distance between the end face of the first cylinder and the end face of the first circular body is not larger than 10 mm. Both the widths of the first circular groove and the second circular groove are between 2 and 8 mm.

Advantages according to embodiments of the invention are summarized as follows:

1. The rock specimens for the pure shear test are a new type of rock specimen, thereby enriching the existing types of the rock for the pure shear test.

2. The shear stress is conveniently and effectively measured based on the common rock mechanics testing system by using the rock specimen and the method of the invention, thereby solving the problem that the existing techniques are unable to realize the real pure shear and pose specific requirements on the testing devices.

3. The rock specimen for the pure shear test of the invention has simple structure and is convenient for manufacture.

BRIEF DESCRIPTION OF THE DRAWINGS

The invention is described hereinbelow with reference to the accompanying drawings, in which.

In the drawings, the following reference numbers are used: 1. Rock body; 2. First cylinder; 3. First circular groove; 4. First circular body; 5. Second circular groove; 6. Second cylinder; 7. Second circular body; H. Distance between a bottom of first circular groove and a bottom of second circular groove; d. Diameters of a first cylinder and a second cylinder; D. Diameter of a rock body having a shape of a cylinder; L. Side length of a rock body having a shape of a regular square prism; $h_1$. Depth of a first circular groove; $h_2$. Depth of a second circular groove; $h_3$. Height of a first cylinder; $h_4$. Distance between an end face of first cylinder and an end face of first circular body; and b. Widths of a first circular groove and a second circular groove.

DETAILED DESCRIPTION OF THE EMBODIMENTS

For further illustrating the invention, experiments detailing a rock specimen and a method for testing pure shear of the same are described below. It should be noted that the following examples are intended to describe and not to limit the invention.

In the following examples, MTS Model 815 rock mechanics testing system was utilized to conduct the pure shear test, and loading rates were 0.001 mm/s, 0.01 mm/s, 0.1 mm/s, 1 mm/s, 5 mm/s, and 7 mm/s.

Example 1

Figure 1:
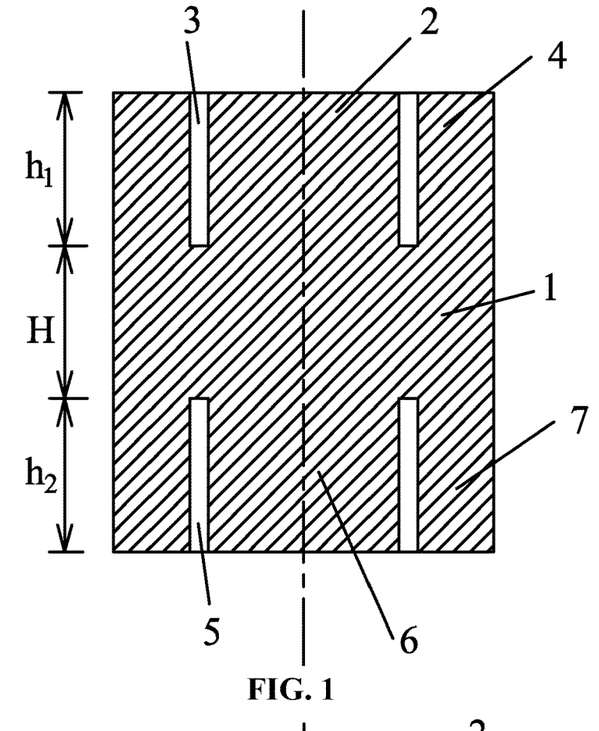
FIG. 1 is a sectional view of a first rock specimen for pure shear test in accordance with one embodiment of the invention.
Figure 2:
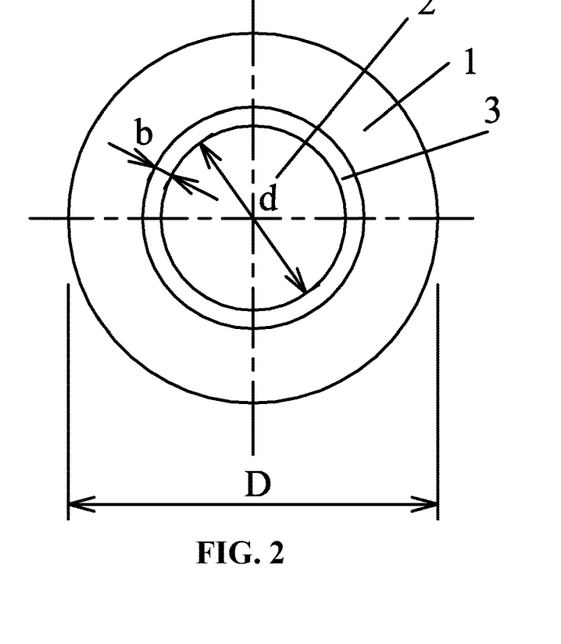
FIG. 2 is a top view of a rock body having a shape of a cylinder of FIG. 1.

A rock specimen for pure shear test, as shown in FIGS. 1-2, a rock body 1 of the rock specimen is in the shape of a cylinder. An upper end face and a lower end face of the rock body are in parallel with each other. A first circular groove 3 is disposed on the upper end face of the rock body 1 and has a circle center coinciding with a center of the rock body 1. A second circular groove 5 is disposed on the lower end face of the rock body 1 and has a circle center coinciding with the center of the rock body 1. The first circular groove 3 divides an upper part of the rock body 1 into a first cylinder 2 disposed at the center and a first circular body 4 surrounding the first cylinder 2. The second circular groove 5 divides a lower part of the rock body 1 into a second cylinder 6 disposed at the center and a second circular body 7 surrounding the second cylinder 6. An end face of the first cylinder 2 and an end face of the first circular body 4 are disposed on a same plane. An end face of the second cylinder 2 and an end face of the second circular body 7 are disposed on a same plane. Dimensions of different components of the rock specimen are as follows:

The rock body 1 has a diameter D of 50 mm. A width of the first circular groove 3=a width of the second circular groove 5=2 mm. A height $h_1$ of the first circular groove 3=a height $h_2$ of the second circular groove 5=10 mm. A distance H between a bottom of the first circular groove and a bottom of the second circular groove is 10 mm. A diameter of the first cylinder 2=a diameter of the second cylinder 6=25 mm. The diameter of the first cylinder 2 is an inner diameter of the first circular groove 3, and the diameter of the second cylinder 6 is an inner diameter of the second circular groove 7.

The pure shear test of the rock specimen is conducted as follows:

1) A circular cushion block 9 is disposed on a test bench of a rock mechanics testing system, in which, an inner diameter of the circular cushion block is 27 mm, and an outer diameter of the circular cushion block is 55 mm.

Figure 7:
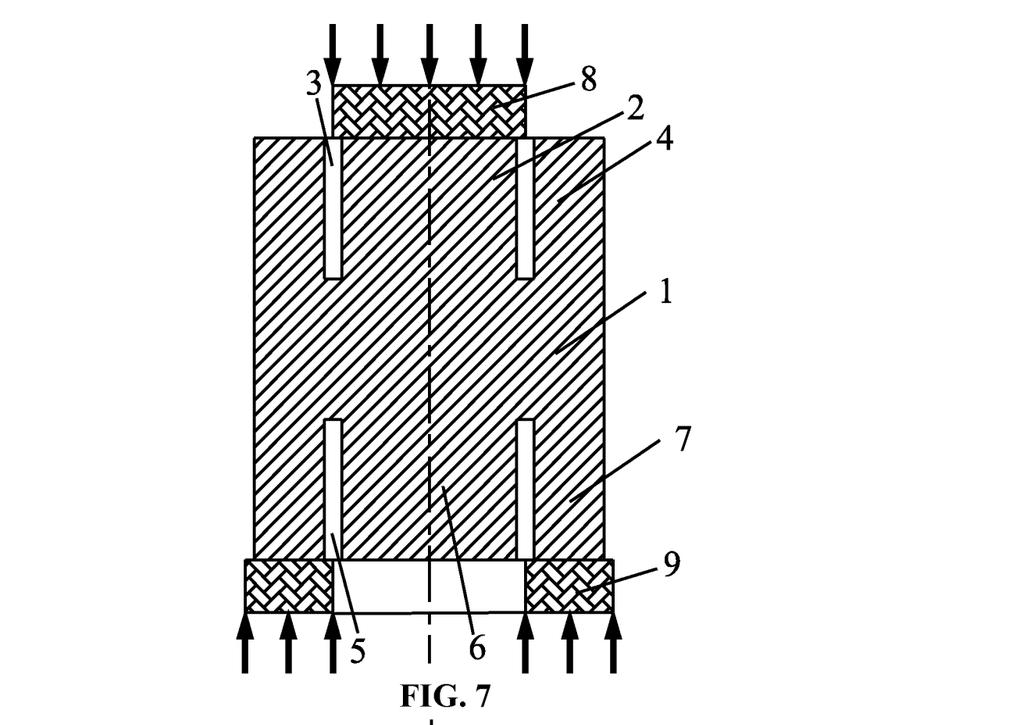
FIG. 7 is a sectional view showing a rock specimen of FIG. 1 mounted on a test bench of a rock mechanics testing system and pressures loaded on the rock specimen.

2) The rock specimen is disposed on the circular cushion block 9 to enable a center line of the rock specimen to coincide with a center line of the circular cushion block 9 and to enable an end face of the second circular body 7 to contact an end face of the circular cushion block 9, as shown in FIG. 7.

3) A cylindrical cushion block 8 is disposed on the end face of the first cylinder 2 of the rock specimen. A diameter of the cylindrical cushion block 8 is 27 mm, and a center line of the cylindrical cushion block 8 coincides with the center line of the rock specimen (as shown in FIG. 7).

Figure 9:
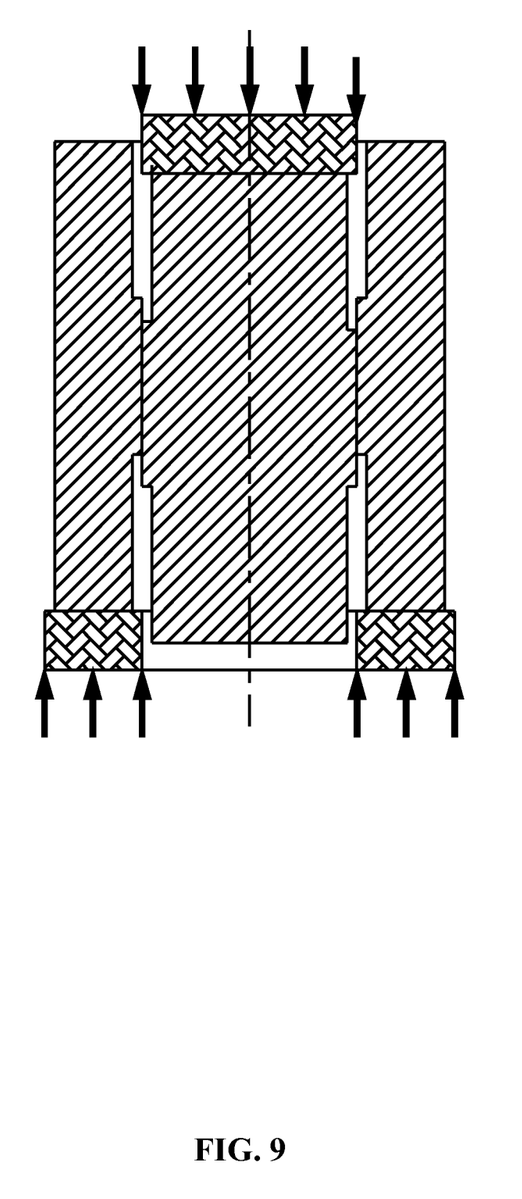
FIG. 9 is a sectional view showing a rock specimen being sheared in pure shear test.

4) The rock mechanics testing system is operated, and pressures are loaded on the rock specimen via the cylindrical cushion block 8 and the circular cushion block 9 (as shown in FIG. 7) to purely shear the rock specimen (as shown in FIG. 9), a loading rate is 0.001 mm/s, and a maximum load F=10 kN.

As shown in FIG. 7, the end face of the first cylinder 2 and the end face of the second circular body 7 are exerted with forces, and a pure shear stress (strength) of the rock specimen to be tested is calculated as follows:

$$\tau = \frac{F}{\pi dH} = \frac{37 \times 1000 N}{3.1415926 \times 25 \times 10 \text{ mm}^2} = 12.73 \text{ MPa}$$

Example 2

A rock specimen for pure shear test is shown in FIGS. 1-2. The rock specimen of this example is the same as that of Example 1 except in the dimensions of different components. In this example, dimensions of the components are as follows:

The rock body 1 has a diameter D of 90 mm. A width of the first circular groove 3=a width of the second circular groove 5=3 mm. A height $h_1$ of the first circular groove 3=a height $h_2$ of the second circular groove 5=20 mm. A distance H between a bottom of the first circular groove and a bottom of the second circular groove is 20 mm. A diameter of the first cylinder 2=a diameter of the second cylinder 6=38 mm.

The pure shear test of the rock specimen is conducted as follows:

1) A circular cushion block 9 is disposed on a test bench of a rock mechanics testing system, in which, an inner diameter of the circular cushion block is 41 mm, and an outer diameter of the circular cushion block is 95 mm.

2) The rock specimen is disposed on the circular cushion block 9 to enable a center line of the rock specimen to coincide with a center line of the circular cushion block 9 and to enable an end face of the second circular body 7 to contact an end face of the circular cushion block 9, as shown in FIG. 7.

3) A cylindrical cushion block 8 is disposed on the end face of the first cylinder 2 of the rock specimen. A diameter of the cylindrical cushion block 8 is 41 mm, and a center line of the cylindrical cushion block 8 coincides with the center line of the rock specimen (as shown in FIG. 7).

4) The rock mechanics testing system is operated, and pressures are loaded on the rock specimen via the cylindrical cushion block 8 and the circular cushion block 9 (as shown in FIG. 7) to purely shear the rock specimen (as shown in FIG. 9), a loading rate is 0.01 mm/s, and a maximum load F=35 kN.

As shown in FIG. 7, the end face of the first cylinder 2 and the end face of the second circular body 7 are exerted with forces, and a pure shear stress (strength) of the rock specimen to be tested is calculated as follows:

$$\tau = \frac{F}{\pi dH} = \frac{35 \times 1000N}{3.1415926 \times 38 \times 20 \, \text{mm}^2} = 14.66 \, \text{MPa}$$

Example 3

Figure 3:
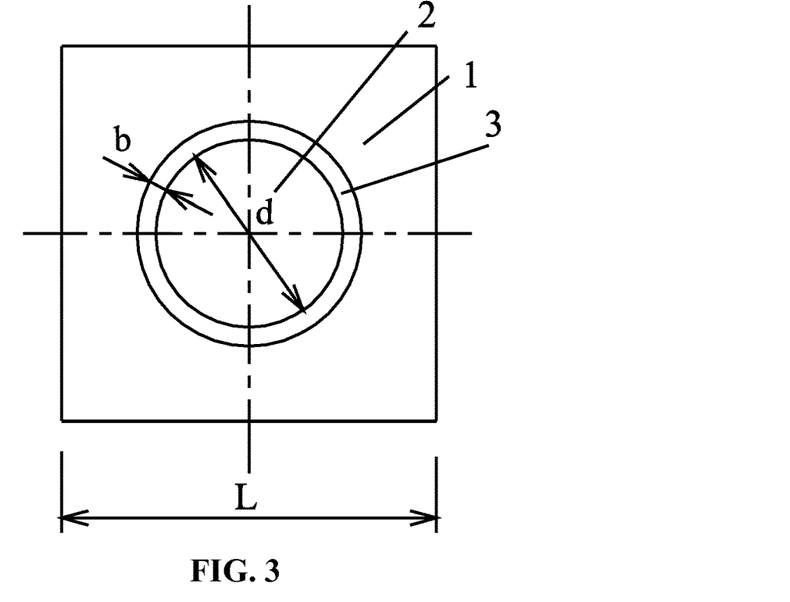
FIG. 3 is a top view of a rock body having a shape of a regular square prism of FIG. 1.

A rock specimen for pure shear test, as shown in FIG. 1 and FIG. 3, is the same as that of Example 1 except in the dimensions of different components and the shape of the rock body 1. In this example, the rock body 1 of the rock specimen is in the shape of a regular square prism, and the dimensions of the components are as follows:

The rock body 1 has a side length L of 120 mm. A width of the first circular groove 3=a width of the second circular groove 5=8 mm. A height $h_1$ of the first circular groove 3 is 25 mm, and a height $h_2$ of the second circular groove 5 is 30 mm. A distance H between a bottom of the first circular groove and a bottom of the second circular groove is 30 mm. A diameter of the first cylinder 2=a diameter of the second cylinder 6=30 mm.

The pure shear test of the rock specimen is conducted as follows:

1) A circular cushion block 9 is disposed on a test bench of a rock mechanics testing system, in which, an inner diameter of the circular cushion block is 38 mm, and an outer diameter of the circular cushion block is 180 mm.

2) The rock specimen is disposed on the circular cushion block 9 to enable a center line of the rock specimen to coincide with a center line of the circular cushion block 9 and to enable an end face of the second circular body 7 to contact an end face of the circular cushion block 9, as shown in FIG. 7.

3) A cylindrical cushion block 8 is disposed on the end face of the first cylinder 2 of the rock specimen. A diameter of the cylindrical cushion block 8 is 38 mm, and a center line of the cylindrical cushion block 8 coincides with the center line of the rock specimen (as shown in FIG. 7).

4) The rock mechanics testing system is operated, and pressures are loaded on the rock specimen via the cylindrical cushion block 8 and the circular cushion block 9 (as shown in FIG. 7) to purely shear the rock specimen (as shown in FIG. 9), a loading rate is 0.1 mm/s, and a maximum load F=37 kN.

As shown in FIG. 7, the end face of the first cylinder 2 and the end face of the second circular body 7 are exerted with forces, and a pure shear stress (strength) of the rock specimen to be tested is calculated as follows:

$$\tau = \frac{F}{\pi dH} = \frac{37 \times 1000N}{3.1415926 \times 30 \times 30 \, \text{mm}^2} = 13.09 \, \text{MPa}$$

Example 4

Figure 4:
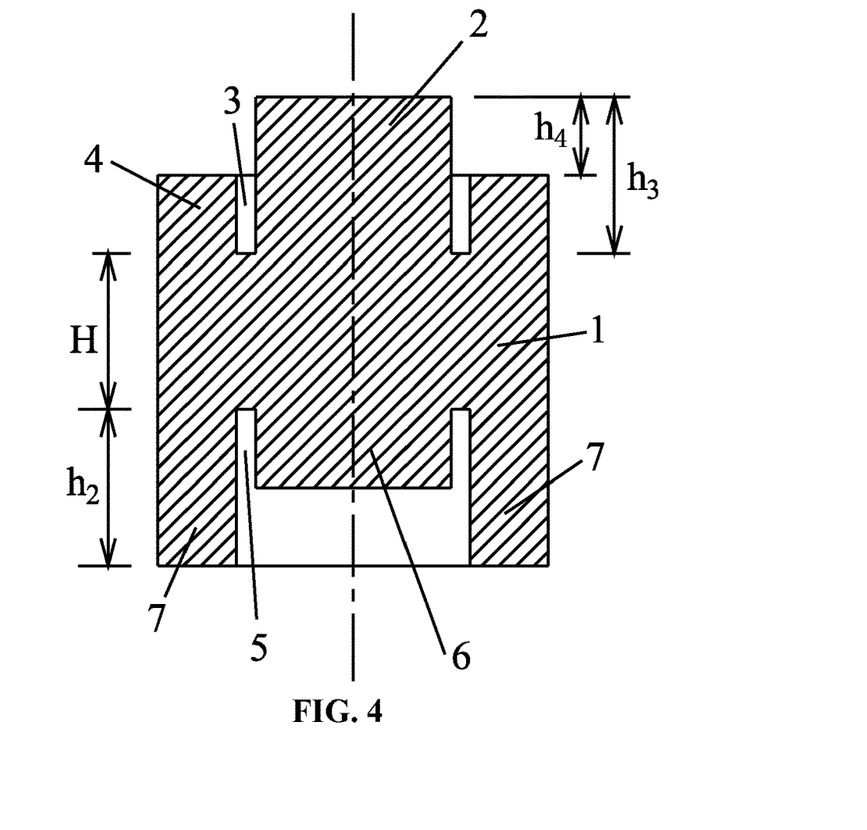
FIG. 4 is a sectional view of a second rock specimen for pure shear test in accordance with one embodiment of the invention.
Figure 5:
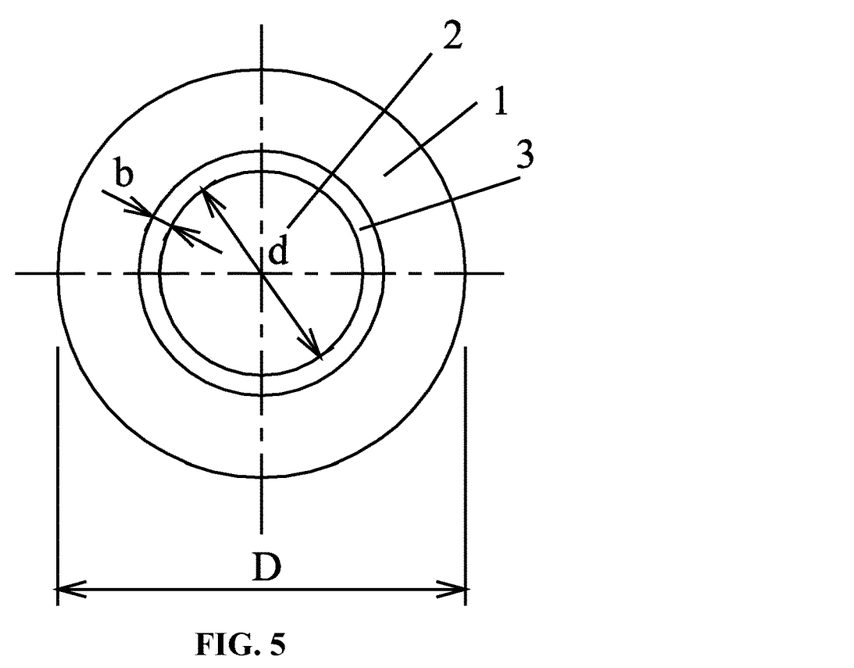
FIG. 5 is a top view of a rock body having a shape of a cylinder of FIG. 4.

A rock specimen for pure shear test, as shown in FIGS. 4-5, a rock body 1 of the rock specimen is in the shape of a cylinder. An upper end face and a lower end face of the rock body are in parallel with each other. A first circular groove 3 is disposed on the upper end face of the rock body 1 and has a circle center coinciding with a center of the rock body 1. A second circular groove 5 is disposed on the lower end face of the rock body 1 and has a circle center coinciding with the center of the rock body 1. The first circular groove 3 divides an upper part of the rock body 1 into a first cylinder 2 disposed at a center and a first circular body 4 surrounding the first cylinder 2. The second circular groove 5 divides a lower part of the rock body 1 into a second cylinder 6 disposed at the center and a second circular body 7 surrounding the second cylinder 6. An end face of the first cylinder 2 is higher than the end face of the first circular body 4, and an end face of the second circular body 6 is lower than an end face of the second circular body 7. Dimensions of different components of the rock specimen are as follows:

The rock body 1 has a diameter D of 100 mm. A width of the first circular groove 3=a width of the second circular groove 5=5 mm. A diameter of the first cylinder 2=a diameter of the second cylinder 6=50 mm. A height $h_3$ of the first cylinder is 40 mm. A distance $h_4$ between the end face of the first cylinder and the end face of the first circular body 4 is 5 mm. A depth $h_2$ of the second circular groove 5 is 35 mm. A height of the second cylinder is 25 mm. A distance H between a bottom of the first circular groove and a bottom of the second circular groove is 40 mm.

Figure 8:
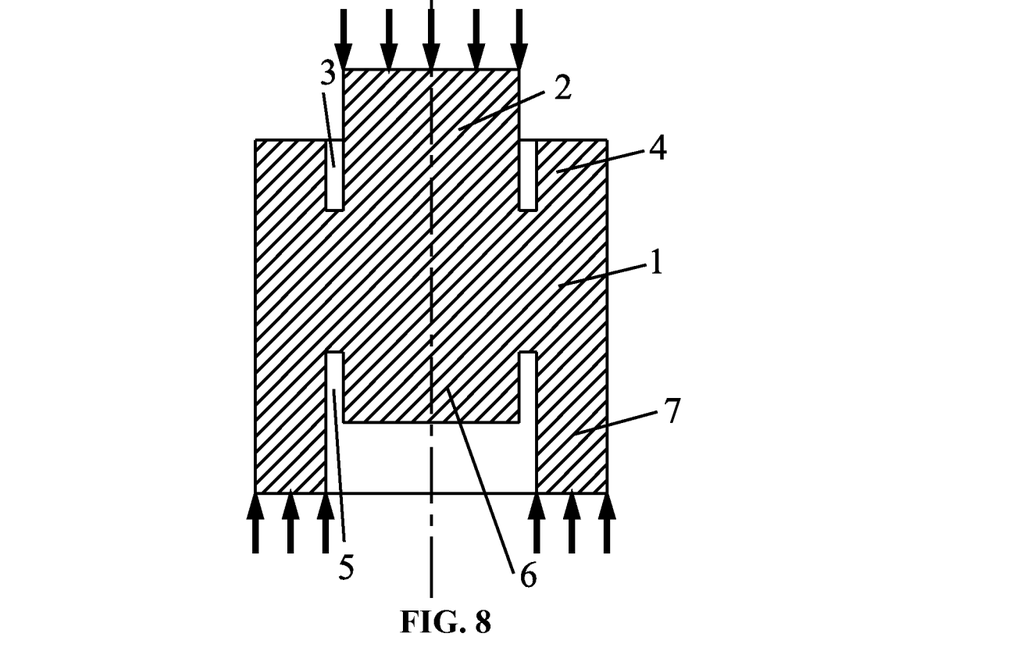
FIG. 8 is a sectional view showing a rock specimen of FIG. 4 mounted on a test bench of a rock mechanics testing system and pressures loaded on the rock specimen.

The pure shear test of the rock specimen is conducted as follows:

1) The rock specimen is disposed on a test bench of a rock mechanics testing system to enable the end face of the second circular body 7 to contact the test bench, as shown in FIG. 8;

2) The rock mechanics testing system is operated, and pressures are loaded on the rock specimen via the end face of the first cylinder 2 and the end face of the second circular body 7 (as shown in FIG. 8) to purely shear the rock specimen, a loading rate is 5 mm/s, and a maximum load F=75 kN.

As shown in FIG. 8, the end face of the first cylinder 2 and the end face of the second circular body 7 are exerted with forces, a pure shear stress (strength) of the rock specimen to be tested is calculated as follows:

$$\tau = \frac{F}{\pi dH} = \frac{75 \times 1000N}{3.1415926 \times 50 \times 40 \text{ mm}^2} = 11.94 \text{ MPa}$$

Example 5

Figure 6:
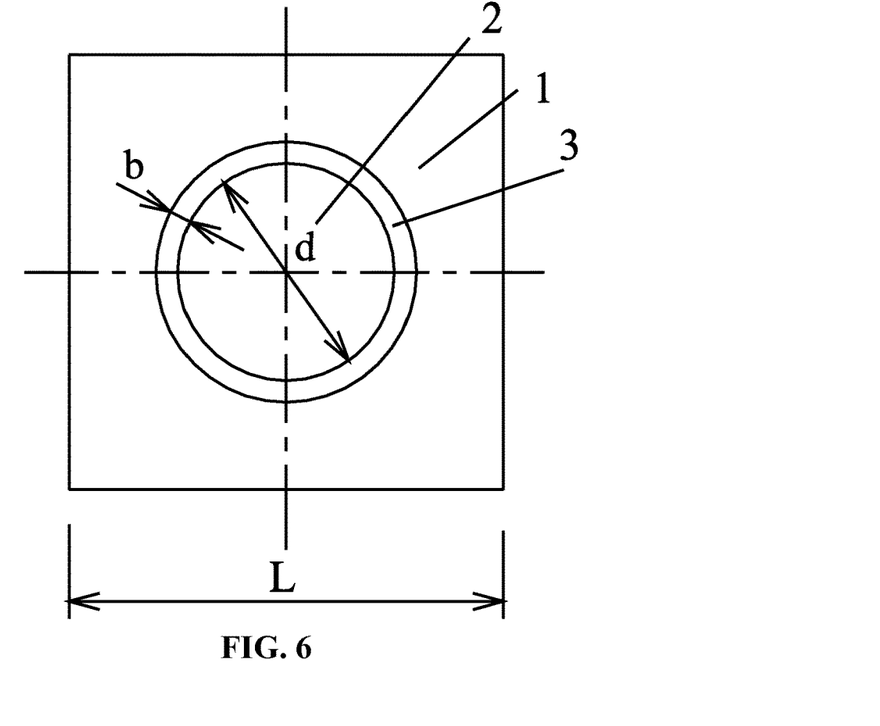
FIG. 6 is a top view of a rock body having a shape of a regular square prism of FIG. 4.

A rock specimen for pure shear test is shown in FIG. 4 and FIG. 6. The rock specimen of this example is the same as that of Example 1 except in the dimensions of different components. In this example, a rock body 1 of the rock specimen is in the shape of a regular square prism, and dimensions of the components are as follows:

The rock body 1 has a diameter D of 80 mm. A width of the first circular groove 3=a width of the second circular groove 5=3 mm. A diameter of the first cylinder 2=a diameter of the second cylinder 6=38 mm. A height $h_3$ of the first cylinder is 16 mm. A distance $h_4$ between the end face of the first cylinder and the end face of the first circular body 4 is 6 mm. A depth $h_2$ of the second circular groove 5 is 40 mm. A height of the second cylinder is 20 mm. A distance H between a bottom of the first circular groove and a bottom of the second circular groove is 25 mm.

The pure shear test of the rock specimen is conducted as follows:

1) The rock specimen is disposed on a test bench of a rock mechanics testing system to enable the end face of the second circular body 7 to contact the test bench, as shown in FIG. 8;

2) The rock mechanics testing system is operated, and pressures are loaded on the rock specimen via the end face of the first cylinder 2 and the end face of the second circular body 7 (as shown in FIG. 8) to purely shear the rock specimen, a loading rate is 7 mm/s, and a maximum load F=40 kN.

As shown in FIG. 8, the end face of the first cylinder 2 and the end face of the second circular body 7 are exerted with forces, a pure shear stress (strength) of the rock specimen to be tested is calculated as follows:

$$\tau = \frac{F}{\pi dH} = \frac{40 \times 1000N}{3.1415926 \times 38 \times 25 \text{ mm}^2} = 13.40 \text{ MPa}$$

Example 6

Figure 10:
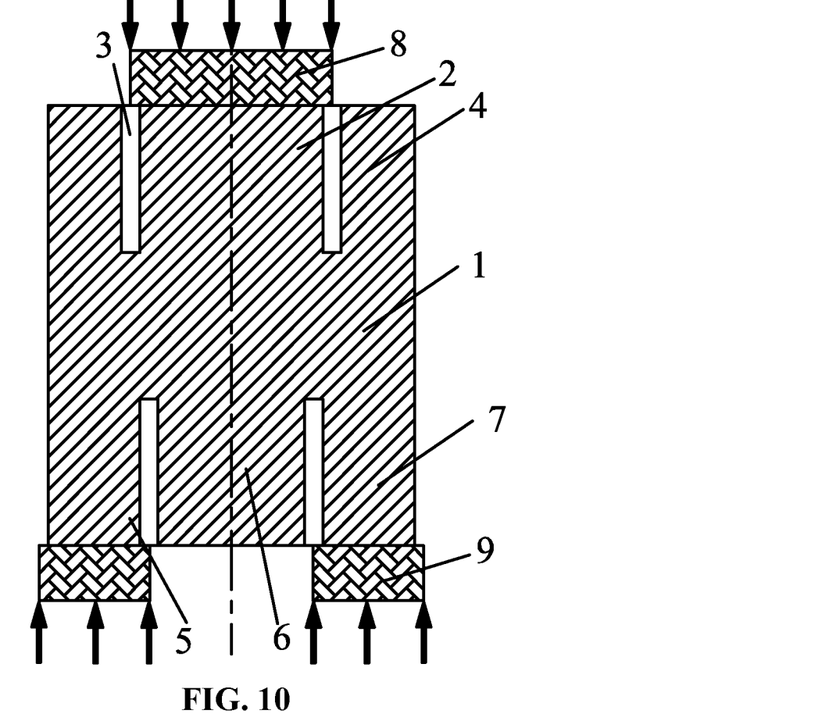
FIG. 10 is a sectional view showing a first rock specimen mounted on a test bench of a rock mechanics testing system and pressures loaded on the rock specimen.
Figure 11:
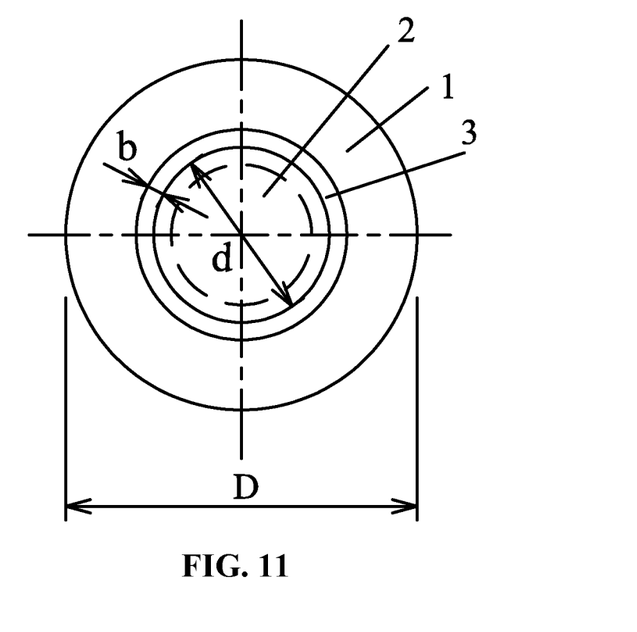
FIG. 11 is a top view showing a rock body having a shape of a cylinder of FIG. 10.

A rock specimen for pure shear test, as shown in FIGS. 10-11, a rock body 1 of the rock specimen is in the shape of a cylinder. An upper end face and a lower end face of the rock body are in parallel with each other. A first circular groove 3 is disposed on the upper end face of the rock body 1 and has a circle center coinciding with a center of the rock body 1. A second circular groove 5 is disposed on the lower end face of the rock body 1 and has a circle center coinciding with the center of the rock body 1. The first circular groove 3 divides an upper part of the rock body 1 into a first cylinder 2 disposed at the center and a first circular body 4 surrounding the first cylinder 2. The second circular groove 5 divides a lower part of the rock body 1 into a second cylinder 6 disposed at the center and a second circular body 7 surrounding the second cylinder 6. An end face of the first cylinder 2 and an end face of the first circular body 4 are disposed on a same plane. An end face of the second cylinder 2 and an end face of the second circular body 7 are disposed on a same plane. Dimensions of different components of the rock specimen are as follows:

The rock body 1 has a diameter D of 50 mm. A width of the first circular groove 3=a width of the second circular groove 5=2 mm. A height $h_1$ of the first circular groove 3=a height $h_2$ of the second circular groove 5=10 mm. A distance H between a bottom of the first circular groove and a bottom of the second circular groove is 10 mm. A diameter of the first cylinder 2 is 25 mm, and a diameter of the second cylinder 6 is 23 mm. The diameter of the first cylinder 2 is an inner diameter of the first circular groove 3, and the diameter of the second cylinder 6 is an inner diameter of the second circular groove 7.

The pure shear test of the rock specimen is conducted as follows:

1) A circular cushion block 9 is disposed on a test bench of a rock mechanics testing system, in which, an inner diameter of the circular cushion block is 25 mm, and an outer diameter of the circular cushion block is 55 mm.

2) The rock specimen is disposed on the circular cushion block 9 to enable a center line of the rock specimen to coincide with a center line of the circular cushion block 9 and to enable an end face of the second circular body 7 to contact an end face of the circular cushion block 9, as shown in FIG. 7.

3) A cylindrical cushion block 8 is disposed on the end face of the first cylinder 2 of the rock specimen. A diameter of the cylindrical cushion block 8 is 27 mm, and a center line of the cylindrical cushion block 8 coincides with the center line of the rock specimen (as shown in FIG. 7).

4) The rock mechanics testing system is operated, and pressures are loaded on the rock specimen via the cylindrical cushion block 8 and the circular cushion block 9 (as shown in FIG. 7) to purely shear the rock specimen (as shown in FIG. 9), a loading rate is 0.001 mm/s, and a maximum load F=10 kN.

As shown in FIG. 10, the end face of the first cylinder 2 and the end face of the second circular body 7 are exerted with forces, and a pure shear stress (strength) of the rock specimen to be tested is calculated as follows:

$$\tau = \frac{F}{\pi dH} = \frac{10 \times 1000N}{3.1415926 \times 25 \times 10 \text{ mm}^2} = 12.73 \text{ MPa}$$

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A rock specimen, comprising a rock body having a shape of a cylinder or a regular square prism, the rock body comprising: an upper part, an upper end face, a first circular groove, a first cylinder, a first circular body, a lower part, a lower end face, a second circular groove, a second cylinder, and a second circular body;

wherein
the upper end face is in parallel with the lower end face;
the first circular groove is disposed on the upper end face of the rock body and has a circle center coinciding with a center of the upper end face of the rock body;
the second circular groove is disposed on the lower end face of the rock body and has a circle center coinciding with a center of the lower end face of the rock body;
a width and an inner diameter of the first circular groove are the same as a width and an inner diameter of the second circular groove;
a distance between a bottom of the first circular groove and a bottom of the second circular groove is between 10 and 40 mm;
the first circular groove divides the upper part of the rock body into the first cylinder located at the center and the first circular body surrounding the first cylinder;
the second circular groove divides the lower part of the rock body into the second cylinder located at the center and the second circular body surrounding the second cylinder; and
a diameter of the first cylinder is the same as a diameter of the second cylinder.

2. The rock specimen of claim 1, wherein an end face of the first cylinder and an end face of the first circular body are disposed on a same plane; and an end face of the second cylinder and an end face of the second circular body are disposed on a same plane.

3. The rock specimen of claim 1, wherein an end face of the first cylinder is higher than an end face of the first circular body; and an end face of the second cylinder is lower than an end face of the second circular body.

4. The rock specimen of claim 2, wherein the distance between the bottom of the first circular groove and the bottom of the second circular groove is between 20 and 30 mm.

5. The rock specimen of claim 4, wherein
both the diameters of the first cylinder and the second cylinder are between ¼ and ½ of a diameter of the rock body having the shape of the cylinder or a side length of the rock body having the shape of the regular square prism;
both the widths of the first circular groove and the second circular groove are between 2 and 8 mm;
a depth of the first circular groove is between 10 and 40 mm; and
a depth of the second circular groove is between 10 and 40 mm.

6. The rock specimen of claim 5, wherein
both the widths of the first circular groove and the second circular groove are between 3 and 5 mm;
the depth of the first circular groove is between 20 and 30 mm; and
the depth of the second circular groove is between 20 and 30 mm.

7. The rock specimen of claim 3, wherein the distance between the bottom of the first circular groove and the bottom of the second circular groove is between 20 and 30 mm.

8. The rock specimen of claim 7, wherein
both the diameters of the first cylinder and the second cylinder are between ¼ and ½ of a diameter of the rock body having the shape of the cylinder or a side length of the rock body having the shape of the regular square prism;
a height of the first cylinder is between 10 and 40 mm;
a distance between the end face of the first cylinder and the end face of the first circular body is not larger than 10 mm; and
both the widths of the first circular groove and the second circular groove are between 2 and 8 mm.

9. A method for testing pure shear of the rock specimen of claim 2, the method comprising:
1) providing a circular cushion block, disposing the circular cushion block on a test bench of a rock mechanics testing system, wherein an inner diameter of the circular cushion block is smaller than an inner diameter of the second circular body or an inner diameter of the first circular body and is larger than a diameter of the second cylinder or a diameter of the first cylinder, and an outer diameter of the circular cushion block is larger than a diameter of the rock body having the shape of the cylinder or a side length of the rock body having the shape of the regular square prism; and providing a cylindrical cushion block, wherein a diameter of the cylindrical cushion block is larger than the diameter of the first cylinder or the diameter of the second cylinder and smaller than the inner diameter of the first circular body or the inner diameter of the second circular body;
2) disposing the rock specimen on the circular cushion block, allowing a center line of the rock specimen to coincide with a center line of the circular cushion block, and allowing the end face of the second circular body or the end face of the first circular body to contact an end face of the circular cushion block;
3) disposing the cylindrical cushion block on the end face of the first cylinder or the end face of the second cylinder, and allowing a center line of the cylindrical cushion block to coincide with the center line of the rock specimen; and
4) operating the rock mechanics testing system, loading a pressure on the rock specimen via the cylindrical cushion block and the circular cushion block to purely shear the rock specimen.

10. The method of claim 9, wherein
both the diameters of the first cylinder and the second cylinder are between ¼ and ½ of the diameter of the rock body having the shape of the cylinder or the side length of the rock body having the shape of the regular square prism;
both the widths of the first circular groove and the second circular groove are between 2 and 8 mm;
a depth of the first circular groove is between 10 and 40 mm; and
a depth of the second circular groove is between 10 and 40 mm.

11. A method for testing pure shear of the rock specimen of claim 3, the method comprising:
1) disposing the rock specimen on a test bench of a rock mechanics testing system, allowing the end face of the second circular body to contact the test bench; and
2) operating the rock mechanics testing system, loading a pressure on the rock specimen via the end face of the first cylinder and the end face of the second circular body to purely shear the rock specimen.

12. The method of claim 11, wherein
both the diameters of the first cylinder and the second cylinder are between ¼ and ½ of a diameter of the rock body having the shape of the cylinder or a side length of the rock body having the shape of the regular square prism;

a height of the first cylinder is between 10 and 40 mm;

a distance between the end face of the first cylinder and the end face of the first circular body is not larger than 10 mm; and both the widths of the first circular groove and the second circular groove are between 2 and 8 mm.

* * * * *